| United States Patent [19] | [11] | 4,341,871 |
|---|---|---|
| Langejan et al. | [45] | * Jul. 27, 1982 |

[54] ACTIVE DRIED BAKER'S YEAST

[75] Inventors: Arend Langejan; Basile Khoudokormoff, both of Delft, Netherlands

[73] Assignee: Gist-Brocades N.V., Delft, Netherlands

[*] Notice: The portion of the term of this patent subsequent to Nov. 23, 1993, has been disclaimed.

[21] Appl. No.: 257,241

[22] Filed: Apr. 24, 1981

Related U.S. Application Data

[63] Continuation of Ser. No. 945,440, Sep. 25, 1978, abandoned, which is a continuation of Ser. No. 836,436, Sep. 25, 1977, abandoned, which is a continuation of Ser. No. 627,836, Nov. 3, 1975, abandoned, which is a continuation of Ser. No. 463,207, Apr. 23, 1974, abandoned, which is a continuation of Ser. No. 133,436, Apr. 12, 1971, abandoned.

[30] Foreign Application Priority Data

Apr. 14, 1970 [GB] United Kingdom ............... 17795/70

[51] Int. Cl.³ .......................... C12N 1/18; A21D 2/00
[52] U.S. Cl. ..................................... 435/256; 426/19; 426/60; 426/62
[58] Field of Search ...................... 426/18, 19, 60, 62; 435/256

[56] References Cited

U.S. PATENT DOCUMENTS

| 3,843,800 | 10/1974 | Langejan | 426/18 |
| 3,993,783 | 11/1976 | Langejan et al. | 426/18 |
| 4,217,420 | 8/1980 | Langejan | 426/62 X |

Primary Examiner—David M. Naff
Attorney, Agent, or Firm—Hammond & Littell, Weissenberger and Muserlian

[57] ABSTRACT

An active dried baker's yeast having a protein content of 47 to 60% and a high gas production is obtained from new yeast hybrids selected from the group consisting of Ng 2031 and Ng 2103. Drying is carried out by dividing fresh compressed yeast into particles and drying the particles to a dry matter content of at least 85% by contacting the yeast with a drying gas at a temperature of not more than 160° C. in not more than 120 minutes so that the temperature of the yeast particles is held between 20° to 50° C. The dried hybrid yeast show a residual activity of at least 85% of the activity of the compressed yeast when incorporated directly into a dough mixture prior to rehydration or at least 70% when rehydrated before addition to other dough components.

5 Claims, No Drawings

ACTIVE DRIED BAKER'S YEAST

PRIOR APPLICATION

This application is a continuation of copending application Ser. No. 945,440 filed Sept. 25, 1978 which in turn is a continuation of copending application Ser. No. 836,436 filed Sept. 25, 1977 which in turn is a continuation of copending application Ser. No. 627,836 filed Nov. 3, 1975 which is a continuation of copending application Ser. No. 436,207 filed Apr. 23, 1974 which is a continuation of copending application Ser. No. 133,436 filed Apr. 12, 1971, all now abandoned.

STATE OF THE ART

Although active dried yeasts are available which are sufficiently active to be used as substitutes for compressed yeasts, their gas production activity is lower than that of the compressed yeasts so that larger quantities of the active dried yeasts than of the compressed yeasts are required to achieve a particular result. Yeasts of high protein content, which have a high activity in the compressed form, are generally unsuitable for use in the dried form as they suffer a drastic loss of activity during drying. Active dried yeasts of good stability have been obtainable without undue loss of activity only from yeasts having a relatively low activity in the compressed form. Thus, of the previously available dried yeasts, none has an activity comparable with the best compressed yeasts.

OBJECTS OF THE INVENTION

It is an object of the invention to provide novel compressed yeast with a protein content of 47 to 60% and an excellent gas production and to provide an improved active dried bakers' yeast.

It is a further object of the invention to provide a novel process for the preparation of an active dried baker's yeast.

It is another object of the invention to provide a novel process for the production of baked goods.

These and other objects and advantages of the invention will become obvious from the following detailed description.

THE INVENTION

According to the invention, yeast hybrids have now been bred which possess good activity in the compressed form and can be dried without undue loss of activity, giving active dried yeasts of high activity, not only after mixing with dry dough components, such as flour, and rehydrating during dough-making, but also when rehydrated separately before addition to other dough components.

The yeast hybrids have a protein content of 47 to 60% (% N×6.25, as determined by the Kjeldahl method), preferably 49 to 55%, based on the dry matter content which, in compressed form, exhibit an activity of at least 550 when determined by the test procedure which consists of suspending a quantity of the compressed yeast corresponding to 450 mg of dry matter in 55 ml of an aqueous solution containing 2 g of sodium chloride at a temperature of 28° C., adding to the suspension 100 g of flour and thereafter mixing the mass for 6 minutes at 28° C., maintaining the dough obtained at 28° C. and measuring the activity as the volume of gas in ml. at 28° C. and 760 mm Hg evolved in the period from 10 to 175 minutes after the start of mixing of the dough; and which yeast hybrids, after conversion to an active dried form having a dry matter content of at least 85%, preferably 90 to 98%, by drying at a maximum temperature of 50° C., have an activity of at least 510 when determined by the test procedure which consists of mixing a quantity of the active dried yeast corresponding to 450 mg of dry matter with 100 g of flour and adding 55 ml. of an aqueous solution containing 2 g of sodium chloride, and thereafter mixing the mass and measuring the activity in the manner hereinbefore specified; and moreover an activity of at least 385 when measured by the test procedure which consists of maintaining a quantity of the active dried yeast corresponding to 450 mg of dry matter in contact with 8 ml of water for 10 minutes at 28° C., mixing the suspension obtained with 100 g of flour and 47 ml of an aqueous solution containing 2 g of sodium chloride, and thereafter mixing the mass and measuring the activity in the manner hereinbefore specified.

In the compressed form (dry matter content about 25–33% by weight), the new hybrids have a high activity. The residual activity of the active dried form amounts to at least 85% of the activity of the compressed yeast when incorporated directly into the dough mixture prior to rehydration, or at least 70% when rehydrated before addition to the other dough components.

Samples of the yeast hybrids exhibiting these properties, designated Ng 2031, and Ng 2103, have been deposited at the "Central Bureau voor Schimmelcultures, Yeast Division" at Delft, The Netherlands, as CBS 6128 and CBS 6131, respectively.

The yeast hybrids of the invention may be cultured in a known manner for the production of bakers' yeast using a nutrient medium containing sugars, such as molasses, with nitrogen being added as ammonium salt and/or ammonia, and phosphate. The propagation can be performed under the usual conditions of temperature and pH in several stages with a final stage consisting of growth under aerobic conditions converting the sugars mainly into yeast. The compressed yeast may be prepared, for instance, by centrifugation and washing of the yeast fermentation liquid and filtration. Since filtration is usually carried out on a vacuum filter, it is preferable to dissolve an osmotically highly active substance such as sodium chloride in the yeast suspension before filtering, and then to wash the osmotic liquid with a solution of lower osmotic pressure, such as tap water, during filtration, as in British Pat. No. 763,926. The compressed yeast, after dividing it into particles, e.g., by extrusion, may be dried in not more than 120 minutes, preferably less than 20 minutes, to a dry matter content of at least 85% by weight, by means of a drying gas flow in such a manner that the yeast particles are held within a temperature range of from 20° to 50° C.

It is advantageous to add a swelling and/or wetting agent to the compressed yeast before drying. Suitable swelling agents are cellulose derivatiges such as methyl cellulose, carboxymethyl cellulose and hydroxypropyl cellulose. Suitable wetting agents are compounds with a hydrophilic and lipophilic group such as esters of saturated or unsaturated fatty acids and suitable alcohols, for instance, sorbitan fatty acid esters, e.g., sorbitan monolaurate, sorbitan monostearate, sorbitan monopalmitate and sorbitan mono-oleate; glycerol fatty acid esters, e.g., glycerol monostearate, glycerol monopalmitate and glycerol distearate; mono- and diglycerides of edible fatty acids modified with lower organic acids such as acetic acid, lactic acid, citric acid, tartaric acid and diacetyl tartaric acid, such as glyceryl stearate lactate; propylene glycol fatty acid esters, e.g. propylene glycol monostearate; or mixtures of two or more of the above-mentioned compounds.

The morphology of the new hybrids in Difco malt extract, or Difco malt agar and in slide cultures on corn meal was determined according to the methods described by Lodder et al. in "The Yeasts" (1952), Chapter II, North Holland Publishing Company, Amsterdam. After 3 days of growth at 25° C. in malt extract, the cells of the new hybrids Ng 2031 and Ng 2103 are spheroical to ovoid, single or in pairs or in short chains or groups. After 1 month at 25° C., a sediment and a ring are formed, but no pellicle or islets. After 3 days of growth at 25° C. on malt agar, the cells are spheroical to ovoid, single, in pairs or in short chains. The streak culture, after one month is cream to yellowish-brown in color, soft, smooth and flat. In the slide cultures, the new hybrids show a more or less well developed pseudomycelium.

Sporulation was studied by incubating a loopful of a 2 days old culture grown on malt agar at 25° C. the inoculum being first washed with sterile 0.3% sodium chloride solution, on the following medium: sodium acetate 0.4% (weight/volume) and agar 1.5% (weight/volume) in tap water, the pH of the medium being adjusted to $6.8 \pm 0.2$ before autoclaving for 20 minutes at 120° C. After 3 to 5 days at 25° C., the strains Ng 2031 and Ng 2103 formed about 25–50% sporulating cells and about 2 to 20% four spore asci. Addition of potassium chloride (1% weight/volume) to the medium had no effect on sporulation.

Carbohydrate fermentation was examined using the method described by Lodder et al. and it was found that in addition to glucose, galactose, sacchrose and maltose, the new hybrids fermented the trisaccharide melezitose within 2 days. Trehalose was fermented within 3 weeks by strain Ng 2031 but not by strain Ng 2103. α-Methylglucoside was quickly fermented by strain Ng 2031 (within 1 to 2 days), especially in the presence of trace amounts of glucose and within one week by Ng 2103.

The requirements of the new hybrids for growth factors were determined according to the method of E. J. Miller, J. Inst. Brewing (1860), Vol. 66, p. 234. Limited growth was observed in the strains when the vitamins $B_1$ and $B_6$ or inositol were omitted from the basic growth medium. Addition of uracil to the same basic medium did not show any significant inhibitory effect.

In the following examples, there are described several preferred embodiments to illustrate the invention. However, it is to be understood that the invention is not intended to be limited to the specific embodiments.

EXAMPLE I

The properties of hybrids Ng 2031 and Ng 2103 of the invention are compared with the properties of yeast strains Ng 720, Ng 732 and Ng 1777. Compressed yeasts were prepared from these strains in a 100,000 liter vessel under the same conditions of pH and temperature, etc., commonly used in this type of propagation under aerobic conditions. At the start of the fermentation, 170 kg of monoammonium phosphate were added. During fermentation, a total of 12,900 kg of molasses and 1380 liters of ammonia (25% $NH_3$ weight/volume) were added, giving a yeast that after drying into the active dried form had a protein content of between 52.0 and 52.9% (% $N \times 6.25$) based on dry matter. The cultures were filtered and washed and the compressed yeasts obtained were mixed with 2% by weight of sorbitan monostearate in the form of an aqueous suspension. Active dried yeasts were obtained by drying the compressed yeasts, divided into particles, in a stream of hot air at a starting temperature of 120° C., which temperature was gradually decreased so that the temperature of the yeast particles themselves did not rise above about 35° C. The over-all drying time was 8 minutes. The active dried yeasts obtained had a dry matter content of 93.0 to 93.9% by weight.

The letters $B^2$, $B^3$ and $B^4$ in Table I refer to the three tests for measuring the activity of yeasts described below:

TEST PROCEDURE

In all three tests $B^2$, $B^3$ and $B^4$ a dough was prepared from an amount of yeast corresponding to 450 mg of dry matter, 100 g of flour and 55 ml of water containing 2 g of NaCl, the water being at a temperature of 28° C. The dough obtained was placed in a water bath adjusted to a temperature of 28° C., and the amount of gas produced was determined during the interval from 10 minutes to 175 minutes after the start of mixing the dough. The volume of gas produced was given in ml at 28° C. and 760 mm Hg.

The tests differ in the method of making the dough. In Test $B^2$, the active dried yeast was mixed with 100 g of flour in a mixer. The salt solution was added and the components were mixed for 6 minutes at 28° C. into a dough. In Test $B^3$, the compressed yeast was suspended in the salt solution, 100 g of flour were added and the components were mixed for 6 minutes at 28° C. into a dough. In Test $B^4$, the active dried yeast was rehydrated for 10 minutes with 8 ml of water at a temperature of 28° C., and the suspension obtained was mixed with 100 g of flour and 47 ml of water containing 2 g of salt. The components were mixed for 6 minutes at 28° C. into a dough. The averaged results of the several tests are given in Table I.

TABLE I

| Yeast | Ng 720 | Ng 732 | Ng 1777 | Ng 2031 | Ng 2103 |
|---|---|---|---|---|---|
| Compressed yeasts | | | | | |
| ml gas evolved in Test $B^3$ | 610 | 554 | 586 | 616 | 610 |
| Active dried yeasts | | | | | |
| Dry matter content (%) | 93.3 | 93.7 | 93.5 | 93.6 | 93.8 |
| Protein content (% N × 6.25) based on dry matter | 52.6 | 52.5 | 52.0 | 52.1 | 52.3 |
| ml gas evolved in Test $B^2$ | 461 | 466 | 499 | 560 | 560 |
| percentage activity $B^2/B^3$ | 75.6 | 84.2 | 85.2 | 91.0 | 91.3 |
| ml gas evolved in Test $B^4$ | | | 333 | 485 | 482 |
| percentage activity $B^4/B^3$ | | | 56.3 | 78.8 | 79.2 |

Thus, yeast Ng 720 (which is used in practice as a good quality compressed yeast) exhibits a good activity in the compressed form, but has only poor activity in the dried form when rehydrated according to test $B^2$ (rehydration after mixing the yeast with flour for making the dough), as evidenced by the low percentage activity of 75.6% (expressed as a percentage of the gas production compared with that of the compressed yeast). Therefore, this yeast is not suitable for the production of an active dried yeast of good quality.

The yeast Ng 732 which is used in practice for the production of conventional active dried yeast, has a relatively poor activity in the compressed form, so that although the ratio of the activities observed in tests $B^2$ and $B^3$ is higher, the absolute activity according to test $B^2$ is low. Therefore, although a better stability to drying and rehydration according to test $B^3$-characterizes this yeast, this yeast is also not suitable for the production of an active dried yeast of good quality.

The yeast Ng 1777 has the high activity in the compressed form needed to obtain a high activity in the active dried form, but the active dried form of this yeast is very sensitive to the rehydration method used, thus, in test $B^2$ a relatively high activity is observed, whereas in test method $B^4$ the activity is low (333), representing only 56.3% of the activity of the compressed yeast observed in test $B^3$.

However, the new yeast hybrids of the invention possess high activities in the compressed form, show after drying according to test $B^2$ a considerably higher activity than that of the yeast Ng 1777, and have a pronouncedly better activity than that yeast in test $B^4$. The new hybrids are thus highly desirable for making active dried yeast.

EXAMPLE II

The hybrid Ng 2103 was propagated in a 100,000 liter vessel and 16,200 kg of molasses, 1770 liters of ammonia and 215 kg of monoammonium phosphate were added. The yeast obtained had a protein content (% $N \times 6.25$) based on dry matter of 53.5% after drying into an active dried form and evolved, as compressed yeast, 661 ml of gas when determined according to test $B^3$. After processing into an active dried yeast in the same manner as in Example I using the same amount of wetting agent, the product obtained had the following properties: dry matter content 93.6%, ml of gas evolved in test $B^2$ were 599 and percentage activity $B^2/B^3$ was 90.6. Continuing the drying process to a dry matter content of 96.6%, the following results were obtained: ml of gas evolved in test $B^2$ were 586, and percentage activity $B^2/B^3$ was 88.6.

Various modifications of the compositions and method of the invention may be made without departing from the spirit or scope thereof, and it should be understood that the invention is intended to be limited only as defined in the appended claims.

We claim:

1. An active dried bakers' yeast having a protein content of 47 to 60% (% $N \times 6.25$, as determined by the Kjeldahl method) based on dry matter content, said dried yeast being obtained from a compressed yeast selected from the group consisting of Ng 2031 and Ng 2103 and having a dry matter content of at least 85% by weight, which exhibits (a) an activity of at least 510 when determined by the test procedure consisting of mixing a quantity of the active dried yeast corresponding to 450 mg of dry matter with 100 g of flour and adding 55 ml of an aqueous solution containing 2 g of sodium chloride and thereafter mixing the mass for 6 minutes at 28° C., maintaining the dough obtained at 28° C. and measuring the activity as the volume of gas in ml at 28° C. and 760 mm Hg evolved in the period from 10 to 175 minutes after the start of mixing the dough; and (b) an activity of at least 385 when measured by the test procedure consisting of maintaining a quantity of the active dried yeast corresponding to 450 mg of dry matter in contact with 8 ml of water for 10 minutes at 28° C., mixing the suspension obtained with 100 g of flour and 47 ml of an aqueous solution containing 2 g of sodium chloride, and thereafter mixing the mass and measuring the activity in the manner specified above, the said yeast being dried by dividing a fresh compressed yeast into particles and drying the particles to a dry matter content of at least 85% by weight by passing therethrough a drying gas at a temperature of not more than 160° C. in not more than 120 minutes with a drying gas flow so that the temperature of the yeast particles are held within a temperature range of 20° to 50° C.

2. An active dried yeast of claim 1 having a protein content of 49 to 55% based on dry matter content.

3. An active dried yeast of claim 1 wherein the dry matter content is 90 to 98% by weight.

4. An active dried yeast of claim 1 wherein the yeast hybrid is NG 2031.

5. An active dried yeast of claim 1 wherein the yeast hybrid is Ng 2103.

* * * * *